(12) United States Patent
Smeekens et al.

(10) Patent No.: US 6,864,051 B1
(45) Date of Patent: Mar. 8, 2005

(54) PLANT GENE CONSTRUCTS AND THEIR USE

(75) Inventors: Sjef Smeekens, Driebergen (NL); Peter Weisbeek, Den Dolder (NL); Marcel Proveniers, Utrecht (NL)

(73) Assignee: Advanta Seeds B.V., Kapelle (NL)

( * ) Notice: Subject to any disclaimer, the term of this patent is extended or adjusted under 35 U.S.C. 154(b) by 0 days.

(21) Appl. No.: 09/423,575

(22) PCT Filed: May 14, 1998

(86) PCT No.: PCT/IB98/00821

§ 371 (c)(1),
(2), (4) Date: Jan. 27, 2000

(87) PCT Pub. No.: WO98/51800

PCT Pub. Date: Nov. 19, 1998

(30) Foreign Application Priority Data

May 14, 1997 (GB) .............................................. 9709789
Dec. 30, 1997 (GB) .............................................. 9727458

(51) Int. Cl.$^7$ .......................... C12Q 1/68; C07H 21/02; A01H 1/00
(52) U.S. Cl. .......................... 435/6; 536/23.1; 800/278
(58) Field of Search ........................... 435/6, 424, 430, 435/69.1; 536/23.1; 800/278, 295

(56) References Cited

U.S. PATENT DOCUMENTS 5,744,693 A * 4/1998 Meyerowitz et al. ....... 800/205

FOREIGN PATENT DOCUMENTS

| WO | WO 96/14414 | * | 5/1996 |
| WO | WO 97/10339 |   | 3/1997 |

OTHER PUBLICATIONS

Quaedvilieg N et al. The homeobox gene ATH1 of Arabidopsis is depressed in the photomorphogenic mutanta cop1 and det1. The Plant Cell, vol. 7: 117–129, 1995.*

Quaedvileg et al. The homeobox gene ATH1 of Arabidopsis is Derepressed in the Photomorphogenic Mutants cop1 and det1. Plant Cell, vol. 7, pp. 117–129, 1995.*

Robson, Paul R.H., McCormac, A.C., Irvine, A.S., and Smith H., "Genetic engineering of harvest index in tobacco through overexpression of a phytochrome gene," Department of Botany, University of Leicester, 14:995–998 (Aug. 1996).

Quaedvlieg, N., Dockx, J., Rook, F., Weisbeek, P., and Smeekens, S., "The Homeobox Gene ATH1 of Arabidopsis Is Derepressed in the Photomorphogenic Mutants cop1 and det1," The Plant Cell 7:117–129 (Jan. 1995).

Lincoln, C., Long, J., Yamaguchi, J., Serikawa, K., and Hake, S., "A knotted1–like Homeobox Gene in Arabidopsis Is Expressed in the Vegetative Meristem and Dramatically Alters Leaf Morphology When Overexpressed in Transgenic Plants," The Plant Cell 6:1859–1876 (Dec. 1994).

Aoyama, T., Dong, C.–H., Wu, Y., Carabelli, M., Sessa, G., Ruberti, I., Morelli, G., and Chua, N.–H., "Ectopic Expression of the Arabidopsis Transcriptional Activator Athb–1 Alters Leaf Cell Fate in Tobacco," The Plant Cell 7:1773–1785 (Nov. 1995).

George, C., Lincoln, C., Hake, S., "KNAT1 Induces Lobed Leaves with Ectopic Meristems When Overexpressed in Arabidopsis," The Plant Cell 8:1277–1289 (Aug. 1996).

Proveniers, M., and Smeekens, S., "The Arabidopsis homeobox gene ATH1 and floral transition," XP–002075918.

* cited by examiner

*Primary Examiner*—Jeffrey Fredman
*Assistant Examiner*—Suryaprabha Chunduru
(74) *Attorney, Agent, or Firm*—Christensen O'Connor Johnson Kindness PLLC

(57) ABSTRACT

A plant gene construct is disclosed comprising a complete or partial DNA sequence coding for an ATH1 gene product under the control of a promoter functional in plants. The promoter is preferably heterologous. Plant cells are transformed with such a plant gene construct, and plants comprising such cells have modified flowering properties. There is further described a process for modifying the flowering process in plants by transforming plants with a construct according to the invention.

4 Claims, 9 Drawing Sheets

FIG. 1

```
        10         20         30         40         50         60
ATTAGTTATAAAATGTTGCTATTTGTGATCTAGTGCTCTGAATCTTTTAGTGAGGCAG
        70         80         90        100        110        120
ATGATGAAGATTATGAATTCTTCATGAAATTATTGTAAGAAAAGAACATAGAGAAGCT
       130        140        150        160        170        180
GCGGAATGAAAGTACACTGTTCTTTCACGGAGAAAGATAAATAAGCATTATCTTCTT
       190        200        210        220        230        240
CTTCAGTTTTTAACACATTTGGAAATTTGATGTAAAAATTCTCTTTGGAACGTTGT
       250        260        270        280        290        300
GTTGTCTGAAATCTTCCCAAAGTTCTATCAGAAGAAGGATAAAGTTTCATAGAAAC
       310        320        330        340        350        360
CCAATGGACAACAACAACAACACACTTTAGTTCTCTGATAATGTCATGACTAAC
       370        380        390        400        410        420
CAAAATCCTCTTCTCATGGATTTATACCTTCAAGAGAAGATTCAACTTCATTCTCAACA
       430        440        450        460        470        480
ATGCTTCCATGGAATACCATCAGATCAGATCCCTACACAAATGGGTGGCTTTGATATTTC
       490        500        510        520        530        540
AATTCTATGCTGACTAACAAATACTTATCATCTTCTCCACGGTCTATCGATGTTCAAGAT
       550        560        570        580        590        600
AACCGCAATGTTGAGTTCATGGCCTCCCTCCCCTCCCATCCTCCACTTCATCCTTTGGAT
       610        620        630        640        650        660
CATTTAAGACACTATGATGATTCCTCAAACAACATGTGGGGTTTTGAAGCAAATAGTGAG
       670        680        690        700        710        720
TTTCAGGCATTTTTCAGGTGTAGTTGGTCCAAGTGAACCAATGATGTCTACATTCGGTGAA
```

FIG. 1 (CONT'D)

```
         730       740       750       760       770       780
GAAGATTTCCCGTTTCTAATTTCGAATAAAGAAACAATGAGCTTTCATTGAGTCTTGCA
         790       800       810       820       830       840
TCAGATGTTCTGATGAATGCTCGGGAGATAAGTCTTTGTGCAGCTACAAGATTAGCCTCA
         850       860       870       880       890       900
GAGCAAGCTTCTTGCAGCAGCAAAGACATTTCTAATAACGTTGTTACTCAAGGTTTCTCT
         910       920       930       940       950       960
CAACTTATATATTGGCTCAAATACCTTCACTCTGTTCAAGAAATACTATCTCATTTCGCC
         970       980       990      1000      1010      1020
GCATACTGCTCGATTATTCATCTCGAGGAACCGAGTCAGGAGCTGCTAGTTCAGCCTTT
        1030      1040      1050      1060      1070      1080
ACTTCACGTTTGAGAATATAACTGAGTTTCTTGATGGTGATTCTAATAACTCGGAGGCG
        1090      1100      1110      1120      1130      1140
GGTTTCGGATCTACATTTCAAAGGAGAGCATTAGAAGCAAAGAAAAACCATCTCTTGGAT
        1150      1160      1170      1180      1190      1200
CTTCTTCAAATGGTGGATGATCGATATAGTCATTGCGTAGATGAGATTCATACGGTTATA
        1210      1220      1230      1240      1250      1260
TCAGCGTTCCATGCTGCAACCGAGTTAGATCCACAGTTACACACCCGGTTTGCCCTCCAA
        1270      1280      1290      1300      1310      1320
ACCGTTTCCTTCTTATACAAGAACCTGAGAGAGAGAATCTGCAATAATATAATCTCTATG
        1330      1340      1350      1360      1370      1380
GGATCTGTATTGGAGAGAGGCAAAGACTCAAGAAACCTCTATGTTCCACCAGCAT
        1390      1400      1410      1420      1430      1440
```

```
TGCCTTCTTCAGCAGCTGAAACGAAAGAACCATCAGATTTGGAGACCTCAACGAGGTTTG
       1450      1460      1470      1480      1490      1500
CCTGAGAAATCTGTTCGGTTCTACGGAATTGGATGTTCCAAAACTTCCTTCACCCTTAC
       1510      1520      1530      1540      1550      1560
CCGAAAGATTCGGAGAAACATCTTCTAGCTATACGAAGTGGCTTGACAAGAAGTCAGGTA
       1570      1580      1590      1600      1610      1620
TCAAACTGGTTTATAAATGCGCGGGTTAGGCTATGGAAGCCGATGATAGAAGAGATGTAT
       1630      1640      1650      1660      1670      1680
GCGGAAATGAACAAGAGGAAGCTCAATAACAGTCACATTCAACCAACGACCAACTCTT
       1690      1700      1710      1720      1730      1740
CGAATGCCAAAATCTGTTATGATGAGCCAAGCAATGCTATAAATAGACAACAATTGTGTT
       1750      1760      1770      1780      1790      1800
TACCAACTTTGTGATAATTAGGCAATTGCTACTCTATGATTGCCCAAAACCTAAACCATG
       1810      1820      1830      1840      1850      1860
TACGACTATCATTACGTATGTTATAATTGTATATACAACTCCTTTATCTTTGACTATTTC
       1870      1880      1890      1900
ATTTTATTAAAAAAAAAAAAAAAAAA
```

FIG. 1(CONT'D)

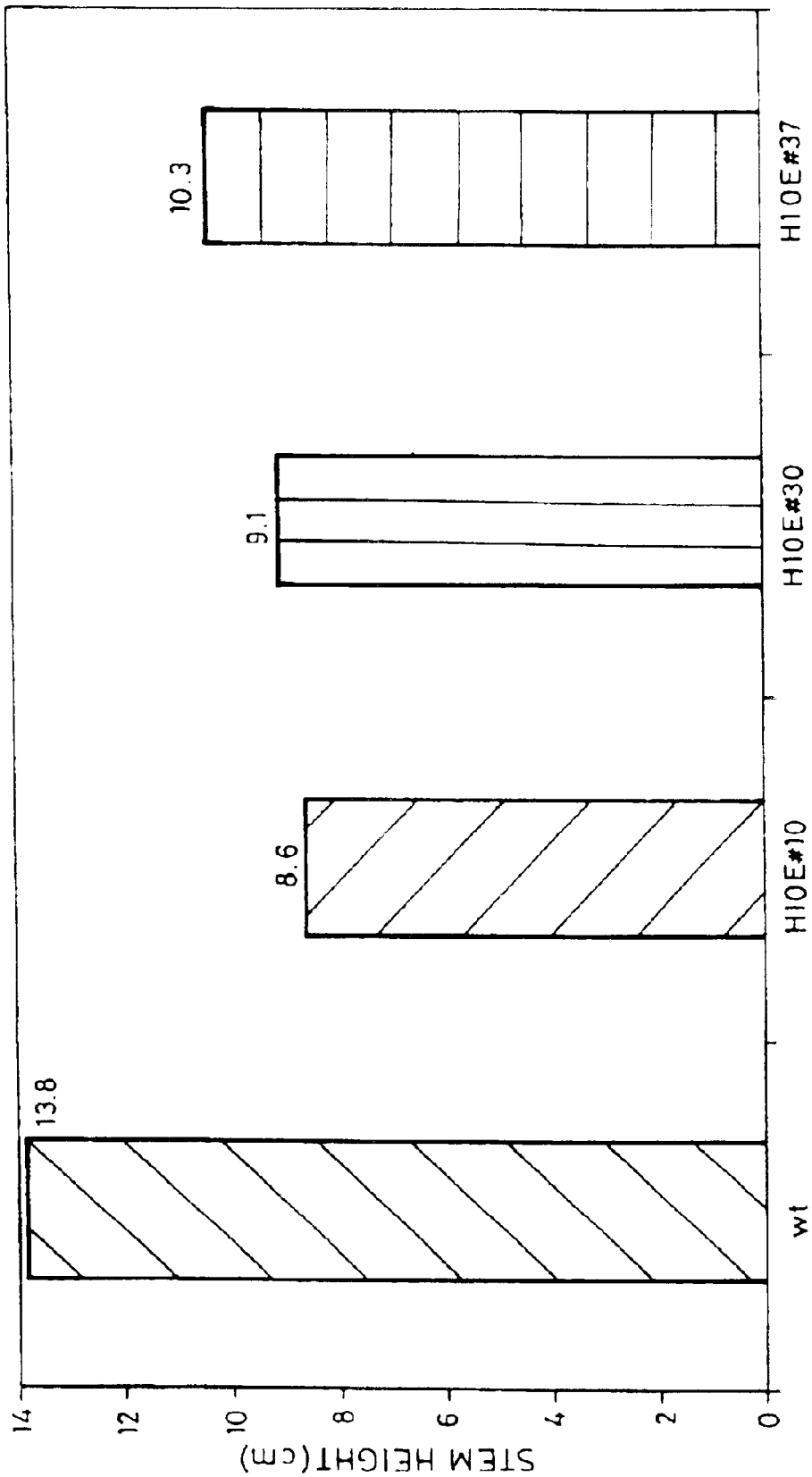
FIG. 5 AtH1 OVEREXPRESSION CAUSES A REDUCTION IN STEM ELONGATION

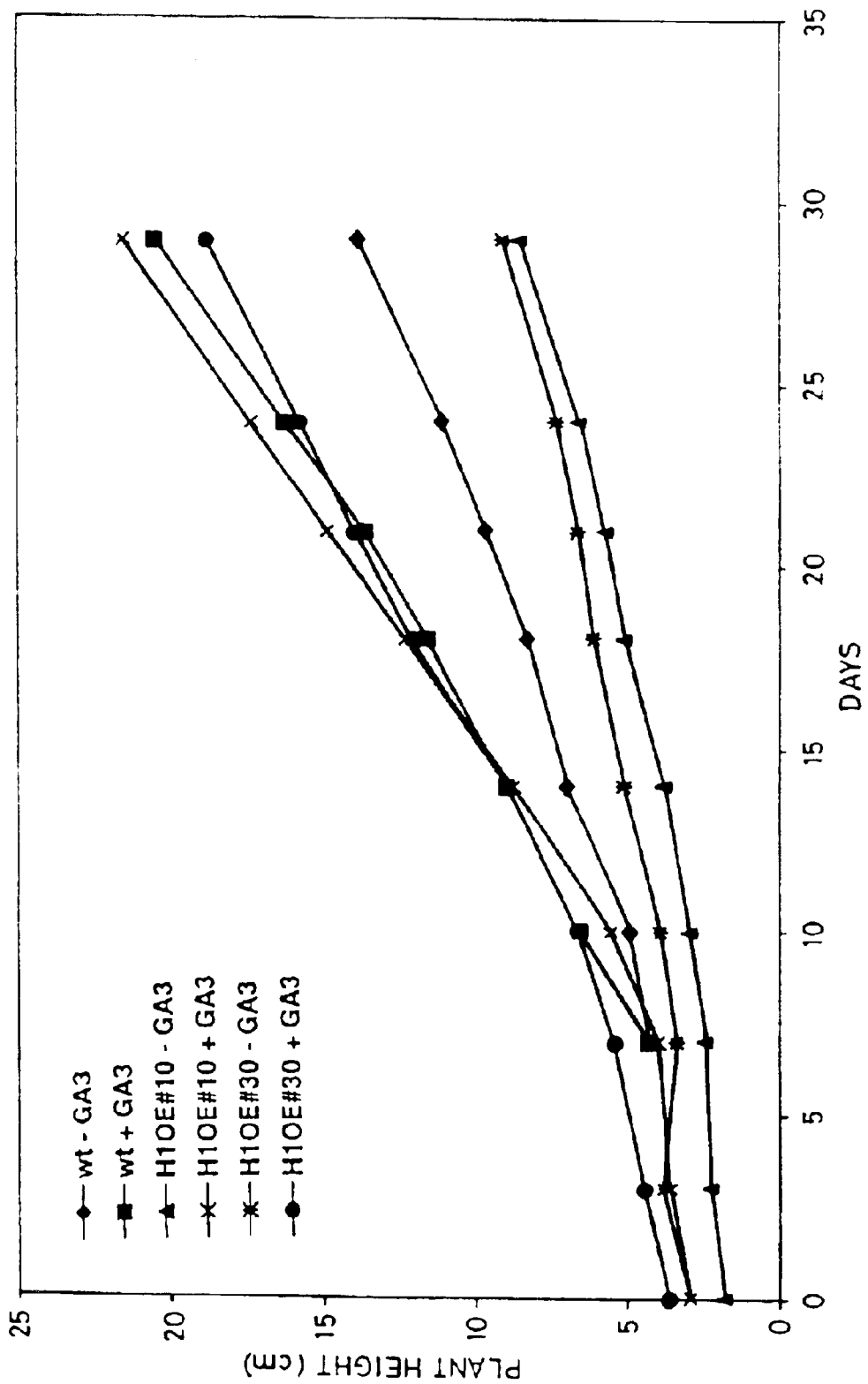
FIG. 6 REVERSION OF AtH1 OVEREXPRESSION PHENOTYPE BY GA3

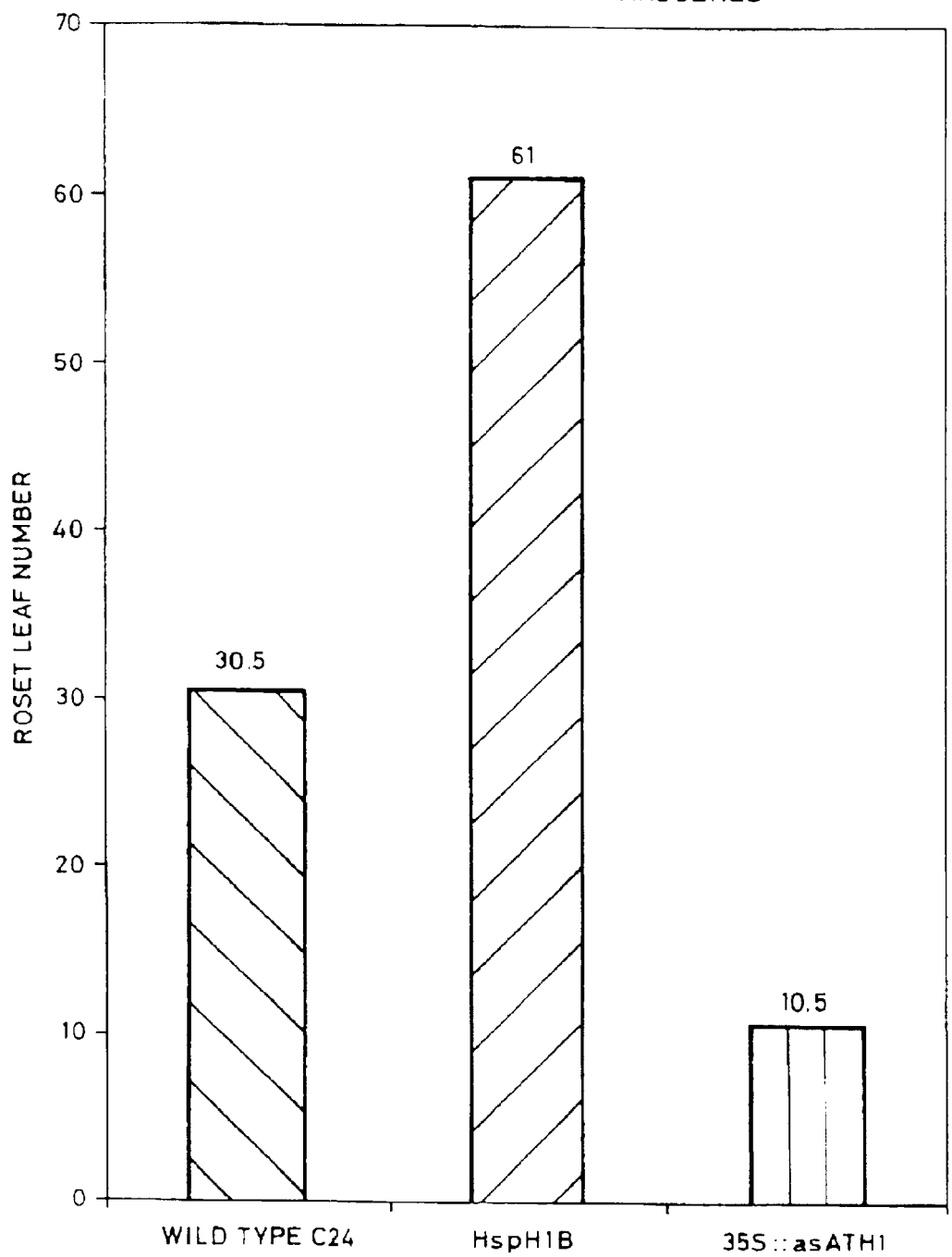

PLANT GENE CONSTRUCTS AND THEIR USE

The present invention relates to novel plant gene constructs, and to their use in controlling the flowering of plants. It further relates to plants containing such constructs.

Plants differ from animals. The adult plant body is formed post-embryonically by the continuous activity of the shoot and root apical meristems. The shoot apical meristem is established during plant embryogenesis and together with cotyledons, hypocotyl, embryonic root and root meristem makes up the basic body plan.

The shoot apical meristem starts as a cluster of about one hundred cells and is the source of the whole aboveground portion of the plant. During the vegetative phase of plant development this meristem gives rise to (a rosette of) leaves, stem, and quiescent axillary meristems. This is followed by the formation of secondary inflorescences, cauline leaves and determinate floral meristems after floral induction. Flowering involves complex interactions of gene products that regulate a switch in shoot meristem identity. Factors determining the expression levels of these genes are genotype and environmental stimuli, such as photoperiod, temperature and light quality. How the transition is affected by these stimuli is still largely unknown.

One of the most important events in the plant life cycle is the decision to enter the reproductive phase. A wide range of environmental and endogenous signals controls this transition of the vegetative phase into the reproductive phase. Important signals are day length, temperature vernalization), nutrient and water availability and several phytohormones esp. gibberellin (GA). These signals induce a shift in vegetative apical meristem identity, named the floral transition, and this transition establishes the inflorescence meristem. Whereas the product of the vegetative apical meristem are leaf primordia, the inflorescence meristem produces primordia that differentiate into secondary inflorescences during early generative development and into flowers later in this stage. In plant breeding research, control of this process is a most important goal for a variety of crops. This is especially true for rosette plants like lettuce, spinach and sugar beet, which show rapid stem elongation (bolting) following the floral transition, and this makes the crop useless.

The transition from vegetative to reproductive growth is a critical developmental event, and because it is the first step of sexual reproduction it is of great importance in agriculture, horticulture, and plant breeding. Farmers may wish to advance or retard the time of flowering, or prevent it altogether: for example to prevent 'bolting' in e.g. lettuces or sugar beet. A better understanding of the molecular biology of plant flowering will allow it to be controlled or influenced in a number of ways, giving important practical benefits to agriculture.

In PCT Publication WO96/14414, use of the Constans (CO) gene to modify flowering mechanisms in plants is disclosed.

The present invention proposes a way of influencing a plant's transition from vegetative to reproductive growth, by providing transformed plants in which the transition is delayed, or brought forward, by expression of specific transgenes influencing this process. Such genes may be constitutively expressed, or expressed only in response to an external stimulus, for example environmental or chemical.

ATH1 is an *Arabidopsis thaliana* homeobox gene. It is described by Quaedvlieg et al., in Plant Cell 7, 117–129, 1995 (herein incorporated by reference): its DNA sequence is given in FIG. 1 of that paper. It was isolated from a light-induced transcription factor collection. It is expressed in young seedlings and flowers. ATH1 mRNA levels in etiolated seedlings are strongly light-dependent (phytochrome) and are also light-adaptive.

We have now established that the protein product of ATH1 is involved in the developmental switch from vegetative to generative growth. As a result of ATH1::GUS studies and initial 35S::ATH1 studies, we have deduced that ATH1 has a function in the transition of the vegetative apical meristem to an inflorescence meristem. Specifically, ATH1 acts as an anti-gibberellin, by repressing GA synthesis or possibly the GA response pathway: Example 6 illustrates this.

Our studies on ATH1::GUS constructs have revealed that in young, light-grown seedlings ATH1 is expressed in all three layers of the shoot apical meristem and leaf primordia. In young, still developing leaves ATH1 is expressed in vascular tissue. This expression disappears in developed leaves. Remarkably, ATH1 meristem expression is restricted to the vegetative phase of development. As soon as *Arabidopsis* starts flowering (vegetative to generative transition) and the shoot apical meristem has become an inflorescence meristem, ATH1 expression in the meristem is downregulated. During the inflorescence phase ATH1 is at a low level expressed in developing vascular tissue of the stem. Later in plant development, when flowers arise, ATH1 is expressed in different parts of the young flower (receptacle, sepals and vascular tissue of stamen). Our hypothesis that ATH1 is involved in controlling the phase transition from vegetative to generative growth is further corroborated by the flowering time phenotypes of ATH1 sense and antisense overexpressors. Plants ectopically overexpressing antisense ATH1 show an early-flowering phenotype: conversely, most plants carrying a sense ATH1 overexpression construct are late flowering. A small proportion of the plants carrying the overexpression construct are, due to ATH1 reduction by co-suppression, early flowering, like the antisense ATH1 over-expressors, and the phenotype of these plants resembles that of the terminal flower mutant (Shannon and Meeks-Wagner, 1991) and the phenotypes of LEAFY— (Weigel and Nilsson, 1995), APETALA 1— (Mandel and Yanofsky, 1995) and CONSTANS (Putteril et al., 1995) over-expressors. Based on these results, combined with the ATH1::GUS data, we deduce that ATH1 is involved in controlling the phase transition from vegetative to generative growth in *Arabidopsis thaliana*, and probably is a flowering time gene.

In consequence, this transition may be promoted by inhibiting the expression of the ATH1 gene: or retarded or prevented by promoting such expression.

Accordingly, the present invention provides a plant gene construct comprising a complete or partial DNA sequence coding for an ATH1 gene product under the control of a promoter functional in plants. The promoter is preferably heterologous. The invention further comprises plant cells transformed with a such a plant gene construct, and plants comprising such cells having modified flowering properties. The invention further comprises a process for modifying the flowering process in plants by transforming plants with a construct according to the invention.

The use of gene sequences to inhibit or promote gene expression is quite well understood. A complete gene sequence, under the control of a promoter that operates effectively in the plant, will generally overexpress the gene product, leading to an amplification of the effect of the protein so produced. Sometimes the gene product is reduced: this phenomenon is termed "co-suppression".

Reduction of the gene product is also generally obtained by using a dominant negative mutation, or by reversing the orientation of the gene sequence with respect to the promoter so that it produces "antisense" messenger RNA.

A DNA construct according to the invention may be an "antisense" construct generating "antisense" RNA or a "sense" construct (encoding at least part of the functional protein) generating "sense" RNA. "Antisense RNA" is an RNA sequence which is complementary to a sequence of bases in the corresponding mRNA: complementary in the sense that A each base (or the majority of bases) in the antisense sequence (read in the 3' to 5' sense) is capable of pairing with the corresponding base (G with C, A with U) in the mRNA sequence read in the 5' to 3' sense. Such antisense RNA may be produced in the cell by transformation with an appropriate DNA construct arranged to generate a transcript with at least part of its sequence complementary to at least part of the coding strand of the relevant gene (or of a DNA sequence showing substantial homology therewith). "Sense RNA" is an RNA sequence which is substantially homologous to at least part of the corresponding mRNA sequence. Such sense RNA may be produced in the cell by transformation with an appropriate DNA construct arranged in the normal orientation so as to generate a transcript with a sequence identical to at least part of the coding strand of the relevant gene (or of a DNA sequence showing substantial homology therewith). Suitable sense constructs may be used to inhibit gene expression (as described in International Patent Publication WO91/08299) or a sense construct encoding and expressing the functional protein may be transformed into the plant to over-express the protein.

DNA constructs according to the invention may comprise a base sequence at least 10 bases (preferably at least 35 bases) in length for transcription into RNA.

There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

As a source of the DNA base sequence for transcription, a suitable cDNA or genomic DNA or synthetic polynucleotide may be used. The isolation of suitable ATH1 sequences from *Arabidopsis* is described in Quaedvlieg et al., above: similar methods may be used to isolate ATH1 sequences from other plants. These may have greater or lesser degrees of homology with ATH1 sequences from *Arabidopsis*. Sequences coding for the whole, or substantially the whole, of the protein may thus be obtained. Suitable lengths of this DNA sequences may be cut out for use by means of restriction enzymes. When using genomic DNA as the source of a partial base sequence for transcription it is possible to use either intron or exon regions or a combination of both.

To obtain constructs suitable for modifying expression of ATH1 in plant cells, the cDNA sequence as found in the protein cDNA or the gene sequence as found in the chromosome of the plant may be used. Recombinant DNA constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence is then cloned into a vector containing upstream promoter and downstream terminator sequences. If antisense. DNA is required, the cloning is carried out so that the cut DNA sequence is inverted with respect to its orientation in the strand from which it was cut.

In a construct expressing antisense RNA, the strand that was formerly the template strand becomes the coding strand, and vice versa. The construct will thus encode RNA in a base sequence which is complementary to part or all of the sequence of the protein mRNA. Thus the two RNA strands are complementary not only in their base sequence but also in their orientations (5' to 3').

In a construct expressing sense RNA, the template and coding strands retain the assignments and orientations of the original plant gene. Constructs expressing sense RNA encode RNA with a base sequence which is homologous to part or all of the sequence of the mRNA. In constructs which express the functional protein, the whole of the coding region of the gene is linked to transcriptional control sequences capable of expression in plants.

For example, constructs according to the present invention may be made as follows. A suitable vector containing the desired base sequence for transcription (such as the pATH1 cDNA clone) is treated with restriction enzymes to cut the sequence out. The DNA strand so obtained is cloned (if desired, in reverse orientation) into a second vector containing the desired promoter sequence and the desired terminator sequence. Suitable promoters include the 35S cauliflower mosaic virus promoter and the tomato polygalacturonase gene promoter sequence (Bird et al, 1988, Plant Molecular Biology, 11:6517662) or other developmentally regulated plant a; promoters. Suitable terminator sequences include that of the *Agrobacterium tumefaciens* nopaline synthase gene (the nos 3' end).

In a DNA construct according to the invention, the transcriptional initiation region may be derived from any plant-operative promoter. The transcriptional initiation region may be positioned for transcription of a DNA sequence encoding RNA which is complementary to a substantial run of bases in a mRNA encoding the ATH1 protein (making the DNA construct a full or partial antisense construct).

The transcriptional initiation region (or promoter) operative in plants may be a constitutive promoter (such as the 35S cauliflower mosaic virus promoter) or an inducible or developmentally regulated promoter, as circumstances require. For example, it may be desirable to modify protein activity at certain stages of the plant's development. Use of a constitutive promoter will tend to affect protein levels and functions in all parts of the plant, while use of a tissue-specific promoter allows more selective control of gene expression and affected functions. Thus the antisense or sense RNA is only produced in the organ in which its action is required.

The DNA constructs of the invention may be inserted into plants to regulate the expression of the ATH1 gene resulting in modification of plant characteristics (in particular flowering). Depending on the nature of the construct, the production of the ATH1 gene product may be increased, or reduced, either throughout or at particular stages in the life of the plant. Generally, as would be expected, production of the protein is enhanced only by constructs which express RNA homologous to the substantially complete endogenous protein mRNAs. Full-length sense constructs may also inhibit protein expression. Constructs containing an incomplete DNA sequence shorter than that corresponding to the complete gene generally inhibit the expression of the gene and production of the proteins, whether they are arranged to express sense or antisense RNA.

A DNA construct of the invention is transformed into a target plant cell. The target plant cell may be part of a whole plant or may be an isolated cell or part of a tissue which may be regenerated into a whole plant. The target plant cell may be selected from any monocotyledonous or dicotyledonous plant species. Plants may be derived from the transformed plant cell by regeneration of transformants and by production of successive generations of the transformants' progeny.

Constructs according to the invention may be used to transform any plant using any suitable transformation technique to make plants according to the invention. Both monocotyledonous and dicotyledonous plant cells may be transformed in various ways known to the art. In many cases such plant cells (particularly when they are cells of dicotyledonous plants) may be cultured to regenerate whole plants which subsequently reproduce to give successive generations of genetically modified plants. Any suitable method of plant transformation may be used. For example, dicotyledonous plants such as tomato and melon may be transformed by Agrobacterium Ti plasmid technology, such as described by Bevan (1984, Nucleic Acid Research, 12:8711–8721) or Fillatti et al (Biotechnology, July 1987, 5:726–730). Such transformed plants may be reproduced sexually, or by cell or tissue culture. Monocots may be transformed by use of the gene gun. Other methods for plant transformation include microinjection and electroporation.

Examples of genetically modified plants according to the present invention include cereals, for example rice and maize, wheat, barley, oats and rye. Other important seed products are oilseed rape (canola), sugar beet, sunflower, soya and sorghum. Most crops are grown annually from seed and the production of seed of any kind depends upon the ability of the plant to flower, to be pollinated and to set seed. In horticulture, control of the timing of flowering is important. Horticultural plants whose flowering may be controlled include lettuce, endive and vegetable brassicas including cabbage, broccoli and cauliflower, and carnations and geraniums.

The main characteristics of modified plants according to the invention are early or delayed flowering. Genotypes in which production of the ATH1 protein is inhibited generally flower early: genotypes in which it is stimulated flower late. Other effects on plant phenotype may also be observed, e.g. dwarf habit, for example in tobacco.

Control of the time of flowering may be useful for several reasons. For example, flowering may be controlled to provide flowers or fruit at the time most appropriate for marketing. In hybrid production, flowering of male and female parents may be co-ordinated. It is most convenient to do this by the use of inducible gene promoters, responsive to external stimuli, for example application of chemicals. An example of such a promoter is the maize glutathione-s-transferase isoform II gene promoter, activated by application of a known herbicide safening agent (WO93/01294 to ICI).

Bolting control may be economically important in several crop species. For example, in sugarbeet, producing varieties which have a reduced tendency to bolt after cold treatment would be of great use. Processing factories could spread their activities over a longer period of time, with significant savings in overheads. Bolting-resistant varieties could be sown very early in the season (February) or even the year before in autumn (provided winter frost was not a problem). Further, varieties in which bolting is increased may be bred faster: crossings may be carried out annually instead of biannually as at present.

Early flowering sunflower would have an extended geographical range. It could be grown further north (north of Paris), and possibly in drier regions, e.g. parts of Spain, avoiding periods of drought later in summer.

In vegetables, bolting may be controlled in for example lettuce and endive. This would allow growing the crop more easily during summer. Existing varieties tend to bolt rather rapidly under summer conditions. In grasses, reduced (or no) bolting is beneficial for fodder types (improved feed quality) and amenity types (better quality lawns).

It will on occasion be of advantage to time the expression of transgenes to stop when flowering starts, or suppress naturally-occurring genes until flowering starts. This may be done using the ATH1 promoter to control expression of a transgene, or transcription of DNA homologous to a natural gene. Accordingly it is a further separate feature of the invention to provide a DNA construct comprising the ATH1 promoter linked to heterologous DNA so as to cause transcription thereof in plant cells: and plant cells transformed with such DNA constructs.

ATH1 is expressed in the vegetative apical meristem, and downregulation of this expression coincides with floral transition. Forced constitutive expression of ATH1 results in a dramatic repression of floral transition both in Arabidopsis and tobacco: thus, in the case of Arabidopsis bolting is postponed. Conversely, repression of ATH1 results in an early flowering phenotype. Our results suggest that ATH1 exerts its function through modulation of GA biosynthesis or responsiveness. We expect the ATH1 gene to be the basis of a particularly useful bolting control system.

Day Length and Floral Transition

The floral transition has been particularly well investigated in Arabidopsis thaliana. This species has become the model system for studying floral transition: at the genetic level through the isolation of flowering-time mutants; and at the molecular level through cloning of genes whose products participate in the control of floral transition. Arabidopsis is a typical rosette plant in which the vegetative leaves are closely spaced due to reduced internode elongation. Upon floral transition the newly formed internodes rapidly elongate ('bolting'). In most Arabidopsis ecotypes day length is of major importance in determining floral transition. Arabidopsis is a facultative long day (LD) plant, which means that floral transition is hastened by long days (16 hours light/8 hours dark cycle), but there is no obligate requirement for it.

Under long day (LD) conditions floral transition is rapidly initiated and only a few rosette leaves are formed (~7 leaves, 16–20 days for the Col-0 ecotype). When grown under short days (SD), e.g. 8 hrs light/16 hrs dark, floral transition takes much longer (~60 days) and a full leafy rosette is formed which can have in excess of ~30 rosette leaves (Col-0 ecotype).

Gibberellic Acid (GA) and Floral Transition

It has been known for a long time that GA treatment promotes floral transition in a variety of plant species. Most species in which applied GA can induce flowering are long-day or cold-requiring plants, and many of these normally grow as rosettes under non-inductive conditions. Moreover, several experiments suggest that endogenous GA levels are involved in controlling floral transition: conditions that induce floral transitions can exert their effect through elevation of endogenous GA levels probably at or near the apical meristem.

Arabidopsis mutants defective in CA biosynthesis (GA series) or insensitive to this hormone (GAI series) show a late flowering phenotype under non-inductive conditions and moreover, the severe GA1-3 mutant is also late flowering under inductive conditions (Wilson et al., 1992).

Involvement of GA in ATH1 Control of Floral Transition

We tested whether exogenous GA can overcome the inhibitory effect of constitutive ATH1 expression in tobacco. Most remarkably, GA spraying was able to 'rescue' the late flowering phenotype in constitutive ATH1 expressers in tobacco. An involvement of GA was also indicated by the reduced internode elongation phenotype in the tobacco ATH1 expressers. These findings suggest that ATH1 functions as a repressor of GA biosynthesis or, alternatively, of GA responsiveness. The dominant effect of ATH1 overexpression on floral transition in combination with the reversion of this effect by exogenously added GA suggests several uses in a variety of crops. This is especially interesting since deregulated expression of ATH1 does not lead to pleiotropic phenotypes and reversion of the overexpression phenotype is complete. Complete rescue means that there will be no problems regarding reproduction or multiplication of ATH1-transformants: thus maintaining the transgenic lines, which can be a serious problem with flowering mutants, is straitforward. Using the GA switch, plants can be reversed to wild-type development at any moment, plants flower normally, and there is a normal seed set.

Accordingly, it is a further feature of the invention to inhibit over-expression of ATH1 in plants genetically modified according to the invention by treating the plants with a gibberellin, for example gibberellin A3 or A4/A7.

Increase of Harvest Index

When plants grow in close proximity, shade-avoidance syndrome, in which plants react to far-red radiation reflected from neighbors, is manifested. This most obviously results in a rapid and dramatic increase in the extension growth of stems and petioles at the expense of leaf growth, storage organ production, and reproductive development. It is known that by overexpression of phyA genes in tobacco the shade-avoidance response can be overcome, resulting in an increased harvest index (Robson et al., 1996). Harvest index is expressed as leaf biomass as a proportion of total biomass. Overexpression of ATH1 in tobacco causes a reduction in stem growth, while leaf growth and number stay unaffected or even increase compared to wild type. As ATH1 overexpression phenotypes and phyA overexpression phenotypes are similar, this suggests using ATH1 overexpression to increase harvest index in crops. The invention will be further described with reference to the following Examples and Experiments, which illustrate certain aspects of our invention: and with respect to the drawings, in which:

FIG. 1 gives the DNA sequence of ATH1 cDNA (SEQ ID NO:1);

FIG. 5 is a bar graph showing the dwarfing caused by constitutive expression of ATH1 in 90 days old tobacco plants;

FIG. 6 is a graph showing the effect of gibberellin treatment on the height of tobacco plants overexpressing ATH1;

FIG. 7 is a bar graph showing flowering time (in terms of number of rosette leaves formed) for under- and overexpressors of ATH1 in comparison with wild-type *Arabidopsis* (C24 ecotype).

GENERAL METHODS

Plant Material and Plant Growth Conditions

Figure 2:
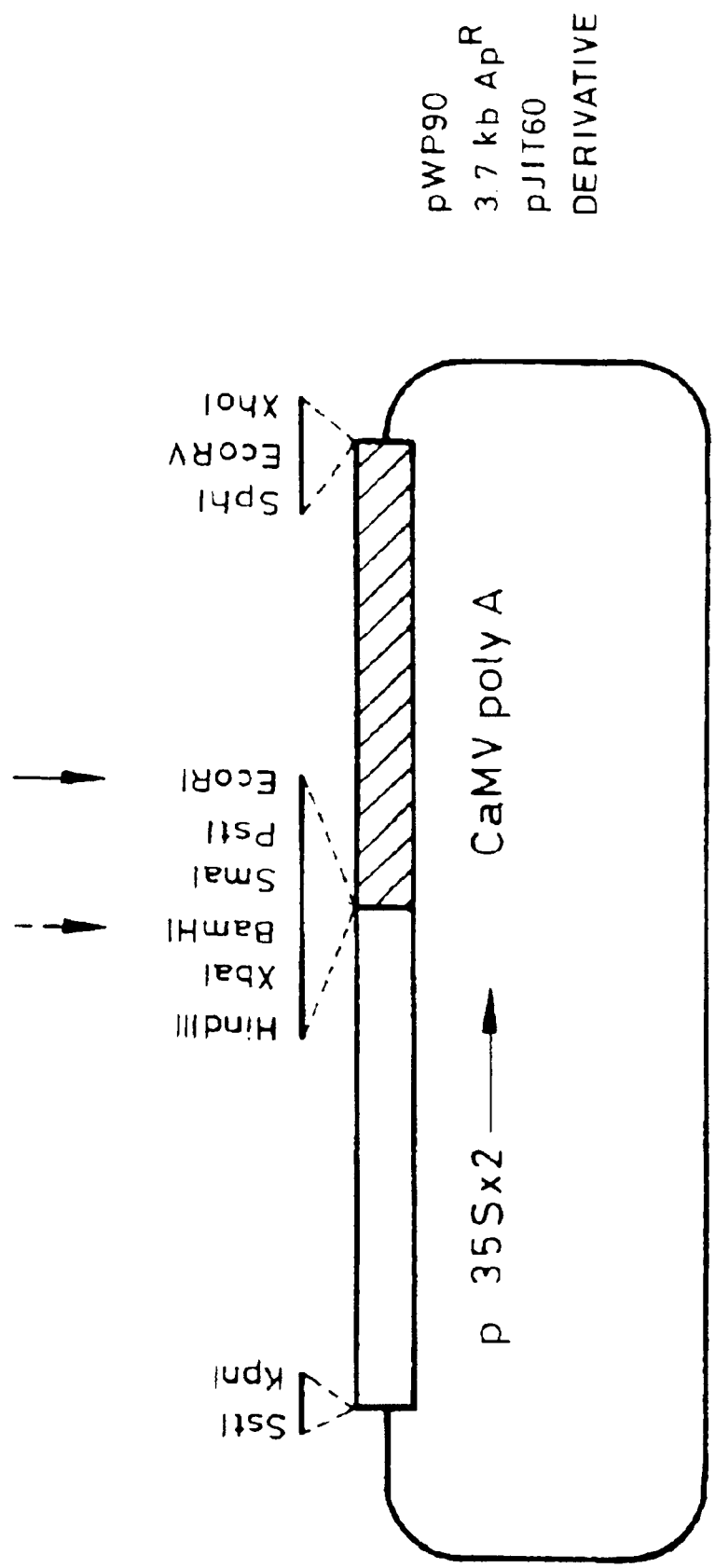
FIG. 2 is a diagram of the plasmid pWP90.

The wild-type genotypes used were *Arabidopsis thaliana* Columbia and C24. The ATH1 gene is located on chromosome 4, between the RFLP markers mi431 (96.9 cM) and 06455 (97.9 cM). *Arabidopsis thaliana* Columbia was used in plant transformation experiments using the vacuum infiltration protocol, while *Arabidopsis thaliana* C24 was used in plant transformation experiments using the root transformation protocol.

Plants were grown in a growth chamber under fluorescent light with a photoperiod of 16 hours followed by an 8 hours dark period at a continuous temperature of 22° C.

To measure flowering time seeds were imbibed and placed at 4° C. for 4 days to break dormancy and were then sown on soil. Germinating seedlings were usually covered with propagator lids for the first 1–2 weeks to prevent dehydration.

Transformation of *Arabidopsis* Plants

Binary constructs containing chimeric ATH1-GUS genes and 35S-antisense ATH1 genes were transformed into *Arabidopsis thaliana* ecotype C24 using the *Agrobacterium tumefaciens*—mediated root transformation method of Valvekens et al. (1988). Transformants were selected on medium containing 50 mg/l kanamycin.

Binary constructs containing chimeric 35S-ATH1 genes were transformed into *Arabidopsis thaliana* ecotype Columbia using the vacuum infiltration protocol (Bent et al. (1994); Bechtold et al. (1993)) with some modifications. Plants were grown separately in 5.5 cm pots. Plants were transformed after appearance of the first siliques on the secondary bolts.

900 ml cultures of *Agrobacterium tumefaciens* containing the appropriate construct were grown the night before the day of infiltration, cells were harvested by centrifugation and resuspended in an equal volume of infiltration medium, containing 2% instead of 5% sucrose. Plants were infiltrated by submerging entire rosettes and bolts for 10 minutes under a vacuum pressure of 100 mm Hg.

Transformant seeds were selected on medium containing 50 mg/l kanamycin.

EXAMPLE 1

ATH1 Expression Analysis

Total RNA Isolation

Total RNA from plants was isolated according to De Vries et al. (1988) with some minor modifications: (1) plant tissue was ground in liquid nitrogen in the presence of half the volume of phenol/extraction buffer and heated to 65° C. in a water-bath and (2) the RNA was ethanol/Na-acetate precipitated before and after LiCl precipitation.

RNAase Protection Analysis

The HindIII-XhoI fragment of phagemid ATH1 was cloned into pBluescriptSK(−) (Stratagene) and digested with HindIII to produce a T7 RNA polymerase template. The ATH1 RNA probe protects a fragment of 140 nt. RNA probe was synthesized by using T7 RNA polymerase (Pharmacia) and buffer as described by the manufacturer, except that 160 µCi of [−$_{32}$P]UTP (800 Ci/mmol) was used. RNAase protection was done by using 10 µg of total RNA and 10 µg of tRNA according to the protocol described by Sambrook et al. (1989). The digested mixture contained 600 units/ml RNAase T1 (Gibco BRL) and 20 µg/ml RNAase A (Boehringer). RNA:RNA hybrids were analyzed by sequence gel electrophoresis (6% polyacrylamide/7M urea) and visualized by autoradiography.

Construction of Chimeric ATH1-GUS Constructs

A SpeI-NcoI fragment containing approximately 1300 nucleotides of ATH1 promoter sequence was isolated. After filling in the NcoI site with Klenow-polymerase, this fragment was inserted into the unique SmaI/XbaI sites of the pBi101.1 binary vector which contains the GUS gene (Jefferson et al., 1987), creating a translational fusion between the ATH1 promoter and the GUS gene. The protein encoded by this chimeric gene consists of 42 aa of ATH1 fused to the GUS protein. The binary construct was called tH1.4. tH1.4 was transformed into competent *Agrobacterium tumefaciens* LBA4404 cells (Gelvin and Schilperoort, 1988). *Arabidopsis* lines (ecotype C24) were transformed as described below.

In Situ Localization of GUS Activity in Transgenic ATH1-GUS *Arabidopsis thaliana* Lines Seedlings and plant tissues were collected and stained for 1 to 16 hours at 37° C. in a solution containing 0.5 mg/ml X-Gluc (Biosynth AG) dissolved in n-dimethyl-formamide, 0,1% Triton X-100, 0.5 mM K4Fe(CN)6.H2O, 0.5 mM K3Fe(CN)6 and 50 mM sodium phosphate buffer, pH 7.2.

Light Microscopy

After X-Gluc staining, plant tissues were fixed overnight in a solution containing 1% glutaraldehyde and 4% formaldehyde in 50 mM sodium phosphate buffer, pH 7.2. Subsequently seedlings were dehydrated in gradual steps: 10%, 30%, 50%, 70%, 90% and 2×100% ethanol. Large plant tissues were pre-embedded first in 1% agarose (Sigma). Infiltration and embedding in Technovite 7100 (Kulzer, Hereaus) was performed as instructed by the manufacturer. 4 μm sections were made on a Reichert-Jung 1140 rotary carrying a disposable Adams steel knife. Sections were stained with 0.1% Ruthenium red (Sigma) in distilled water for 2 minutes at room temperature and photographed on a Zeiss Axioskop using Kodak Professional Ektar 25 film.

Seedlings were fixed and dehydrated as above. Technovit 7100 was infiltrated for 1 day. The seedlings were then transferred to a construction of celluloid transparency (Amovis), double-sided tape, transparency, double-sided tape. In the latter three layers a central region was excised to contain the seedling. Subsequently the seedlings were added in Technovit 7100 solution and the central region was covered by another transparency. Upon overnight polymerisation at room temperature a plastic platelet containing the seedling was obtained. In order to section embedded seedlings in the platelet, the celluloid sheet material was removed and the platelet was cut to allow longitudinal sectioning of relevant seedling regions. Sectioning, staining and photographing was performed as described above.

Localization of ATH1 Expression

The expression of the ATH1 gene was analyzed using RNA-ase protection analysis (Quaedvlieg et al., 1995). High levels of ATH1 mRNA were detected during early seedling development (days 2–6) and in flowers of mature *Arabidopsis* plants. The cellular localization of ATH1 gene expression was determined by introduction of the chimeric ATH1-GUS construct tH1.4 in *Arabidopsis thaliana*. Different tissues were stained with X-gluc, and whole mount preparations and tissue sectioning were made to visualize GUS activity (see below).

ATH1 Expression During Vegetative Development

The shoot apex of a 5-day-old light-grown seedling is flat and consists of a two-layered tunica enclosing the subjacent corpus. At this stage, the meristem has initiated the primordia of the first leaf pair (Mischke and Brown, 1965).

In plants transformed with tH1.4, high levels of GUS activity were present in the shoot apex. Sectioning of the shoot apex showed that the high GUS activity is shown in all three layers of the shoot apical meristem and extends through the subapical region, proceeding down to where the vascular strand of the hypocotyl branches into the cotyledons. High levels of GUS activity were also present in the primordia of the first leaf pair.

ATH1 Expression During Floral Transition and Inflorescence Development

Initially, during the inflorescence phase, the shoot apical meristem gives rise to stem, cauline leaves and secondary inflorescences. As inflorescence development proceeds, the inflorescence meristem produces flower primordia. In plants transformed with tH1.4, GUS activity was downregulated in the inflorescence meristem during the transition phase. There was no GUS activity detectable in the meristem. Low levels of GUS activity were present in the rib zone. Later when flowers arose, GUS activity was present in different parts of the young flower (receptacle, sepals and vascular tissue of stamen).

EXAMPLE 2

Construction of Promoter Fusions to the ATH1 Open Reading Frame

The ATH1 cDNA is cloned into the unique EcoRI/XhoI restriction sites of the well-known and commercially available pBluescript SK(−) vector (Stratagene).

2.1. A CaMV 35S Promoter Fusion to the ATH1 Open Reading Frame.

Figure 3:
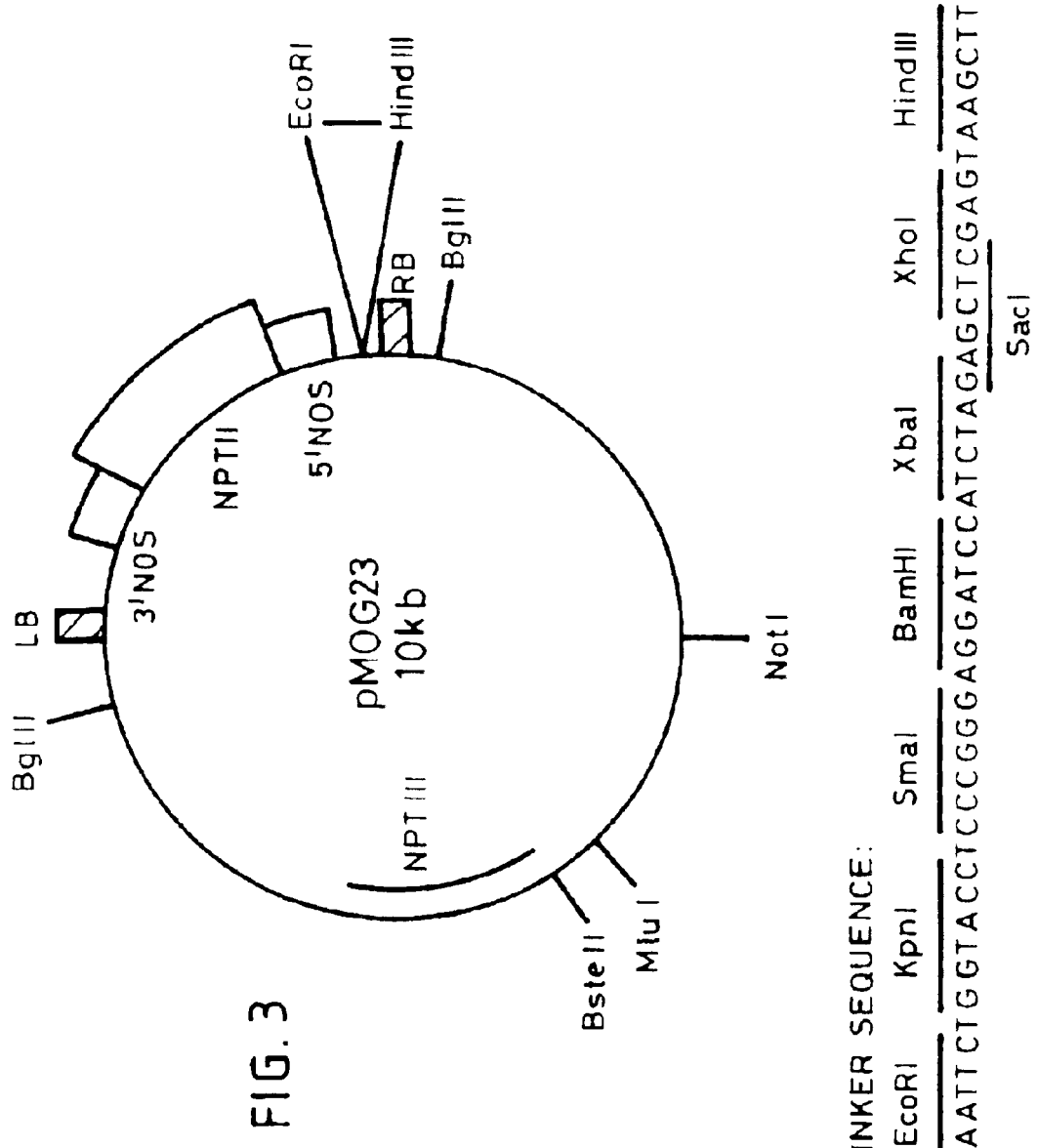
FIG. 3 is a diagram of the plasmid pMOG23 showing the polylinker sequence (SEQ ID NO:2)

A BamHI/SnaBI fragment containing 1573 nucleotides of ATH1 cDNA sequence (the BamHI site was created by PCR mutagenesis, 35 nucleotides downstream of the translation start) was isolated and inserted into the unique BamHI/SmaI cloning sites of pWP90-vector, which contains a double 35S CaMV promoter and a NOS terminator (see FIG. 2), resulting in a transcriptional fusion between the double 35S CaMV promoter and ATH1 cDNA. This construct, called cH1.24, was then cut with SstI/EcoRV restriction enzymes, followed by insertion of the resulting SstI/EcoRV insert in the unique SstI/SmaI restriction sites of binary vector-pMOG23 (see FIG. 3). The binary construct was called tH1.2. tH1.2 was transformed into competent *Agrobacterium tumefaciens* pGV2260 cells (Caplan et al., 1985) cells. *Arabidopsis* lines (ecotype Col-0) were transformed via vacuum infiltration as described below.

2.2 Construction of a CaMV 35S Promoter Fusion to the Antisense ATH1 Frame

An EcoRI/SnaBl fragment containing approximately 1830 nucleotides of ATH1 cDNA sequence was isolated and inserted into the unique SmaI/EcoRI cloning sites of pWP90 vector (see FIG. 2), resulting in a transcriptional fusion between the double CaMV 35S promoter and the antisense ATH1 frame. The resulting construct was called cH1.22. An EcoRV/SstI insert of cH1.22 was then cloned into the unique SmaI/SacI restriction sites of the binary vector pMOG23 (MOGEN)(see FIG. 3). This binary construct, called tH1.1, was transformed into competent *Agrobacterium tumefaciens* LBA4404 cells. *Arabidopsis* lines (ecotype C24) were transformed as described below.

2.3. A Heat Shock Promoter Fusion to the ATH1 Open Reading Frame

By PCR mutagenesis, an additional BamHI site was created in pTT19, a vector containing the promoter, leader and 77 nucleotides of coding sequence of the *Arabidopsis thaliana* Hsp18.2 heat shock gene (Takahashi and Komeda, 1989). The additional BamH1 site is located in the Hsp18.2 untranslated leader at nucleotide −710 of the Hsp18.2 translational start.

By restriction digestion with BamHI the 5' untranslated leader and 77 nucleotides of Hsp18.2 coding sequence were removed. The remaining construct was called leaderless pTT19. A HindIII/BamHI fragment of this leaderless pTT19, containing only Hsp18.2 promoter sequence, was fused to a BamHI/EcoRI fragment containing the entire ATH1 cDNA sequence, which results in a transcriptional fusion of Hsp18.2 promoter with ATH1 5' untranslated leader and coding sequence. The BamHI and EcoRI sites were created by PCR mutagenesis, resulting in a BamHI restriction site at the beginning of the ATH1 cDNA sequence and a EcoRI restriction site immediately downstream of the TAA stop codon. The resulting HindIII/EcoRI fragment was inserted into the unique HindIII/EcoRI restriction sites of pWP90 vector. (see FIG. 2) and this new construct was then partially digested with HindIII and EcoRV restriction enzymes. The largest HindIII/EcoRV restriction fragment was then inserted into HindIII/SmaI cut binary vector pBIN 19 (Frisch et al., 1995). This construct was called HspHl.

A transcriptional fusion between Hsp18.2 promoter and ATH1 coding sequence without leader sequence was also made. In ATH1 cDNA an extra BamHI site was created by PCR mutagenesis immediately upstream of the translational start. Digestion of this BamHI site combined with digestion of the unique XhoI site in ATH1 cDNA results in an fragment of approximately 680 nt, containing ATH1 coding sequence. This fragment of 680 nucleotides was swapped with an approximately 980 nucleotides large fragment that is formed after digestion of HspHl with BamHI/XhoI restriction enzymes. This results in HspHlB, a transcriptional fusion between leaderless ATH1 coding sequence and the Hsp18.2 promoter.

Both HspHl and HspHlB were transformed to competent *Agrobacterium tumefaciens* LBA4404 cells. *Arabidopsis* lines (C24 ecotype) were transformed as described below.

2.4 Fusion of the Pea Plastocyanin Promoter to the ATH1 Open Reading Frame

Figure 4:
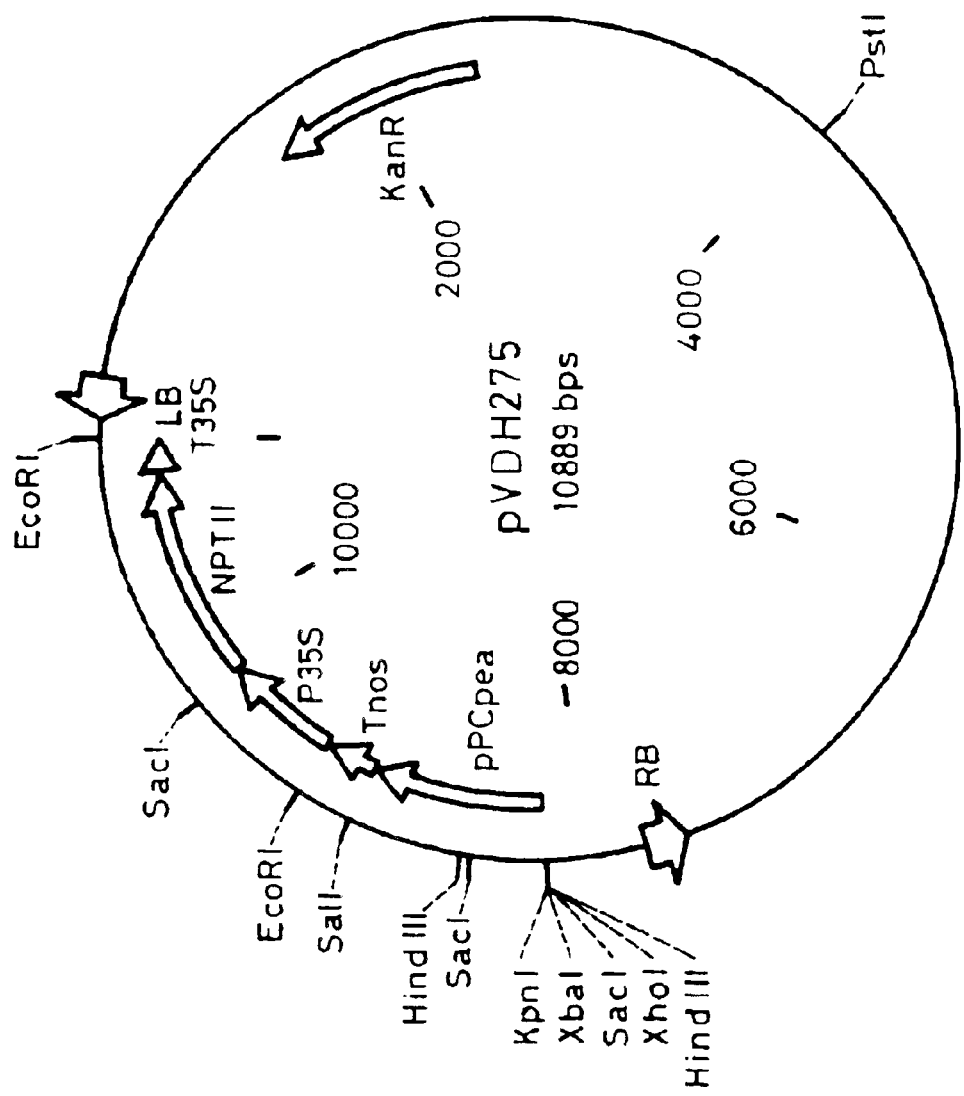
FIG. 4 is a diagram of the plasmid pVDH275.

A transcriptional fusion between pea plastocyanin promoter and ATH1 coding sequence can be made by insertion of ATH1 coding sequence into the unique BamHI and SalI resriction sites of pVDH275 (Pwee and Gray, 1993; Last and Gray, 1989) (see also FIG. 4). In ATH1 coding sequence additional SalI (immediately upstream of ATH1 start ATG) and 3 in BamHI (immediately after ATH1 stop TAA) restriction sites can be created by PCR mutagenesis. The resulting construct in which ATH1 coding sequence is inserted between pea plastocyanin promoter and *Agrobacterium* nos terminator, can be transformed to *Agrobacterium tumefaciens* cells, followed by plant transformation.

Introduction of Extra ATH1 Copies in *Arabidopsis*

Extra copies of ATH1 can be introduced in *Arabidopsis* plants by transforming them with extra ATH1 loci containing ATH1 promoter and ATH1 coding sequence. This can be done by fusion of the approximately 1000 nucleotides large SnaBI/NcoI fragment of ATH1 cDNA to the approximately 250 nucleotides large SstI/EcoRI restriction fragment of pBI101.1, containing the *Agrobacterium* nos terminator (Jefferson et al., 1987). The resulting fragment can be fused to the approximately 3.5 Kb large NcoI restriction fragment of ATH1 genomic clone (Quaedvlieg et al., 1995). The so formed approximately 4750 nucleotides large NcoI/EcoRI fragment, containing ATH1 promoter, ATH1 coding sequence and nos terminator, can be inserted into NcoI/EcoRI cut pMTL23 cloning vector (Chambers et al., 1988). A StuI/EcoRI restriction fragment of the resulting construct can then be inserted into EcoRI/SmaI cut pMOG23 binary vector, *Agrobacterium* cells can be transformed, subsequently followed by plant transformation.

EXAMPLE 3

Influencing Flowering Characteristics Using a CaMV 35S Promoter/ATH1 Gene Fusion Measurement of Flowering Time Flowering time was measured by counting the number of leaves, excluding the cotyledons, in the rosette at the time the flower bud was visible. A close correlation between leaf number and flowering time has been previously demonstrated (Koorneef et al., 1991; Bagnall (1993)).

Overexpression of ATH1 Leads to Delayed Flowering.

In order to gain more insight into the role of ATH1 in plant development, the full length ATH1 cDNA sequence was fused to the constitutive 35S promoter of cauliflower mosaic virus and the 35S::ATH1 chimeric gene so produced was transformed into *Arabidopsis* Col-0 ecotype via the vacuum infiltration method. Six independent primary transformants were obtained.

All these transgenic lines were selfed. From each independent transgenic line 40 individual seeds were germinated on soil and scored for altered phenotypes compared to wild-type plants. Four out of six lines showed a phenotype altered in respect of flowering time. In three of these lines all plants were late flowering (about 14 rosette leaves up to flowering compared with about 10 rosette leaves in wild-type Col-0 plants). In the remaining line about 85% of the plants showed this same late flowering phenotype, while 15% of the plants showed an early flowering phenotype (after about 7 rosette leaves), as tested due to the absence of ATH1 RNA. These early flowering plants also show a terminal flower phenotype, often with incomplete flowers and mutant flower organs.

EXAMPLE 4

Early Flowering by Antisense Expression of ATH1

Like ectopic overexpression of ATH1, inhibiting the ATH1 gene function can also can be used to influence time of flowering. Inhibition of gene function was effected by constitutive overexpression of antisense ATH1.

Full length antisense ATH1 cDNA was fused to the constitutive 35S promoter of cauliflower mosaic virus and the 35S::antisense ATH1 chimeric gene so produced was transformed into *Arabidopsis* C24 ecotype via the Valvekens root transformation protocol. Twenty-two independent transformants were obtained and all of them were selfed. From each line 10 individual seeds were germinated on soil and scored for altered phenotypes compared to wild-type C24 plants. In five of these lines, the plants showed an early flowering phenotype: flowering started after formation of between six and ten rosette leaves compared to about twenty leaves in wild-type plants.

EXAMPLE 5

Altering Flowering Time in *Nicotiana tabacum* by Overexpression of ATH1

As in *Arabidopsis*, ectopic overexpression of ATH1 cDNA (driven by the 35S promoter of cauliflower mosaic virus) in tobacco (*Nicotiana tabacum* cv. Samsun) also led to a delay in flowering time compared to wild-type tobacco. In 35S::ATH1 tobacco plants, flowering was delayed by weeks or months. These plants were also dwarfed. This dwarf habit, like the flowering phenotype, is clearly correlated with the level of expression of the transgene. In the severest case plants did not flower at all and only reached one-fifth of their normal height, whereas in less severe cases plants were delayed in flowering for only one or two weeks and reached about four-fifth of their normal height. Leaf number and shape were normal in all these transformed plants.

EXAMPLES 6-8

The following Examples illustrate the effect of GA on transgenic plants according to the invention. As noted above, ATH1 overexpression effectively represses bolting (floral induction). We hypothesised that ATH1 may be a repressor of GA synthesis or the GA response pathway (we think the former). The following Examples demonstrate and support this hypothesis.

General Methods

Tobacco plants (*Nicotiana tabacum* L. cv. Samsun NN) were transformed using the leaf disk procedure (Horsch et al., 1985). Transgenic plants were selected on MS-medium (Murashige and Skoog, 1962) containing 300 mg/ml kanamycin and 2% sucrose. After transfer to soil plants were grown in a greenhouse at 22° C. under a light regime of 16 hours daylight when necessary supplemented with artificial light. The effects of gibberellin (GA) were tested by foliar applications (spraying) of 100 mM GA3 in a solution containing 100 ml/l of Triton X-100. Control plants were sprayed with a solution containing only 100 ml/l of Triton X-100. Spraying began 60 days after sowing when the wild-type plants were approximately 5 cm tall and the 35S CaMV::ATH1 plants approximately 2.5 cm tall, and continued at 3- to 4-day intervals. Plant height was measured every 3 to 4 days and this will be continued until the onset of flowering, as determined by the appearance of flower primordia.

EXAMPLE 6

Constitutive Overexpression of Sense ATH1 Leads to Delayed Flowering.

6.1 ATH1 Over-expression in Tobacco

In order to express the ATH1 gene constitutively in transgenic plants, its coding region was put under the control of the 35S CaMV promoter and the resulting construct was transformed to tobacco (*Nicotiana tabacum* cv. Samsun NN). Forty independent kanamycin-resistant plants were obtained, of which only five showed detectable transgene expression. ATH1 mRNA levels varied from high in HlOE#4, #10 and #30 plants to intermediate/low levels in HlOE#35 and #37 plants. Depending on ATH1expression level, flowering of these plants was delayed by weeks up to months, when compared to wild-type plants, which flower after 3–5 months depending on the season. In the severest case (HlOE#4) plants never flowered until senescence (>15 months after sowing). HlOE#10 and #30 plants, which show high ATH1 expression, flowered after 15 months, while plants showing the intermediate/low overexpression, HlOE#35 and 37, did not flower until after 6 months. As well as altered flowering-time phenotype, ATH1 overexpressor plants show reduced stem growth, resulting in dwarfed plants. Here there is a clear correlation between severity of she dwarf growth phenotype and the level of transgene expression (see FIG. 5). In the severest case plants only reach about one-fifth of their normal height. The leaf number varies from two times higher than wild type to normal in all transgenes.

6.2 ATH1 Overexpression can be Reversed by GA3

ATH1 overexpression phenotypes can be reversed to a wild-type phenotype by application of GA3. Foliar application of GA3 to the tobacco plants of Example 6.1 (spraying of 100 mM GA3 at three to four day intervals) results in complete restoration of the wild-type stem length (FIG. 6). This holds also true for the late-flowering phenotype (data not shown).

EXAMPLE 7

ATH1 Over-expression in *Arabidopsis*

In order to gain more insight into the role of ATH1 in plant development, the full length ATH1 cDNA was fused to the constitutive 35S promoter of cauliflower mosaic virus and the 35S::ATH1 chimeric gene was transformed into *Arabidopsis* via the vacuum infiltration method. Six independent primary transformants could be obtained and all transgenic lines were selfed. From each independent transgenic line 40 individual seeds were germinated and scored for altered phenotypes compared to wild type plants. Four out of six lines showed an altered phenotype in respect of flowering time. Seeds from these lines did not germinate well and if they did plants were arrested in a seedling stage. Both effects could be overcome by transferring the plants to growth medium containing 10-5 M GA3 and growing them on this medium for three days. Once rescued and transferred to soil plants developed normally, except for a late flowering phenotype. Under short day conditions transgenic plants form much more rosette leaves (vegetative leaves) than wild type plants (about 40 rosette leaves and 100 days after germination, and plants are still not flowering, compared to about 30 rosette leaves in wild-type plants until flowering). Under LD conditions in most of these plants a partial generative to vegetative reversion occurs, shown by the formation of aerial rosettes (vegetative leaves) on the inflorescence stem. Plants (C24 ecotype) containing an extra copy of the ATH1 cDNA under control of the Hsp18.2 heat shock promoter (HspHlB plants) also show a late-flowering phenotype. Even without a heat shock (it is known that this promoter has a basal activity without induction) plants harboring this construct flower much later under LD conditions than wild-type plants (30.5 rosette leaves formed in wild-type vs. 61 rosette leaves formed in HspHlB plants—see FIG. 7).

EXAMPLE 8

Early Flowering by Antisense Expression of ATH1

Like ectopic overexpression of ATH1, knocking out the ATH1 gene function can also give insighta into the function of ATH1 in plant development. Knocking out gene function was established by constitutive overexpression of antisense ATH1. Full length antisense ATH1 cDNA was fused to the constitutive 35S promoter of cauliflower mosaic virus and the 35S::antisense ATH1 chimeric gene was transformed into *Arabidopsis* C24 ecotype via the Valvekens root transformation protocol. Twenty-two independent transformants were obtained and all of them were selfed. From each line 10 individual seeds were germinated on soil and scored for altered phenotypes compared to wild type C24 plants. In five of these lines plants showed an early-flowering phenotype: flowering started after formation of about ten rosette leaves compared to about thirty leaves in wild type plants (see FIG. 7).

EXAMPLE 9

Shade Avoidance Response

When plants grow in close proximity shade avoidance syndrome, in which plants react to lowered red/far-red ratios of light caused by filtering out red light by leaf canopy, is manifested. This results in a rapid and dramatic increase in the extension growth of stems and petioles at the expense of leaf growth, storage organ production, and reproductive development, thereby causing a decrease in harvest index (where harvest index is expressed as lea biomass as a proportion of total biomass).

The shade avoidance response is thought to be predominantly mediated by phytochrome B and overexpression of phytochrome has been shown to eliminate the shade avoidance response, resulting in an increase of harvest index of field-grown tobacco (Robson et al., 1996).

Lack of phytochrome B also leads to loss of shade avoidance response and under inductive conditions this even results in a reduction of stem elongation compared with non-inductive conditions.

In the laboratory, situations causing the shade avoidance response can mimicked by addition of different fluence rates of far-red light (Frc) to continuous white light (Wc). Under these conditions wild-type *Arabidopsis* plants (C24 wt) show a typical shade avoidance response (elongated hypocotyls in Wc+Frc compared with hypocotyl length in Wc only), whereas the phytochrome B photoreceptor mutants, which lack the shade avoidance response, exhibited an opposite response (decrease of hypocotyl length). The antisense AtH1 plants also show a reduction in hypocotyl length and in the most severe antisense plants (asAtH1#3) this reduction is similar to that seed in phyB mutants. So, it can be concluded that like lack of active phytochrome B loss of Ath1 results in loss of the shade avoidance response.

Shade avoidance analysis of antisense AtH1 plants (asAtH1), C24 wild-type plants (C24 wt) and the phy B photoreceptor mutant (phyB) is listed below. Seedlings where grown for 2 days in continuous white light followed by 4 days in the same light regime or by 4 days in white light supplemented by far-red light. The hypcototyl length was measured after 6 days of growth. The following results were generated.

| | | | | |
|---|---|---|---|---|
| C24 wt | Wc | = | hypocotyl length | 5.5 mm |
| | Wc + Frc | = | hypocotyl length | 7.5 mm |
| Phy B | Wc | = | hypocotyl length | 9.5 mm |
| | Wc + Frc | = | hypocotyl length | 7.3 mm |
| Anti-sense AtH1#3 | Wc | = | hypocotyl length | 9.0 mm |
| | Wc + Frc | = | hypocotyl length | 5.0 mm |
| Anti-sense AtH1#7 | Wc | = | hypocotyl length | 9.8 mm |
| | Wc + Frc | = | hypocotyl length | 8.0 mm |
| Anti-sense AtH1#23 | Wc | = | hypocotyl length | 7.5 mm |
| | Wc + Frc | = | hypocotyl length | 7.0 mm |

LITERATURE CITED

Bagnall, 1993: Ann. Bot. 71:75–83
Bechtold et al., 1993: C. R. Acad. Sci. Paris, Life Sciences 316:1194–1199
Bent et al., 1994: Science 265:1856–1960
Caplan et al., 1985: J. Bacteriology 161:655–664
Chambers et al., 1988: Gene 68:139–149
Frisch et al., 1995: Plant Mol. Biol. 27:405–409
Gelvin and Schilperoort, 1988: Plant Molecular Biology Manual: Dordrecht: Kluwer Academic Publisher.
Jefferson et al., 1987: EMBO J. 6:3901–3907
Koorneef et al., 1991: Mol. Gen. Genet. 229:57–66
Last and Gray, 1989: Plant Mol. Biol. 12:655–666
Mandel and Yanofski, 1995: Nature 377:523–524
Putteril et al., 1995: Cell 80:847–857
Pwee and Gray, 1993: Plant J. 3:437–449
Quaedvlieg et al., 1995: The Plant Cell 7:117–129
Shannon and Meeks-Wagner, 1991: The Plant Cell:877–892
Takahashi and Komeda, 1989: Mol. Gen. Genet. 219:365
Takahashi et al., 1992: Plant J. 2:751–761
Weigel and Nilsson, 1995: Nature 377:495–500
Horsch, R., Fry, F., Hoffman, N., Eichholtz, D., Rogers, S. and Fraley, R. (1985). A simple and general method for transferring genes into plants. Science 227, 1229–1231.
Murashige, T. and Skoog, F. (1962). A revised medium for rapid growth and bioassays with tobacco tissue cultures. Physiol. Plant. 15, 473–479.
Robson, P. R. H., McCormac, A. C., Irvine, A. S., and Smith, H. (1996). Genetic engineering of harvest index in tobacco through overexpression of a phytochrome gene. Nature Biotechnology 14(8), 995–998.
Wilson, R. N., Heckman, J. W., and Sommerville, C. R. (1992). Gibberellin is required for flowering in *Arabidopsis thaliana* under short days. Plant. Phys. 100, 403–408.

We claim:

1. A process for modifying flowering in plants comprising generating transformed plants with a construct comprising a DNA sequence coding for an ATH1 gene product under the control of a promoter functional in plants, wherein the gene product is encoded by the nucleotide sequence of SEQ ID NO. 1 and modifies flowering in plants.

2. A process as claimed in claim 1 whereby the flowering process in plants is promoted by transforming the plants using a construct that inhibits the production of ATH1 protein, wherein the ATH1 protein is encoded by the nucleotide sequence of SEQ ID NO. 1.

3. A process as claimed in claim 2 in which the construct is adapted to express RNA antisense to RNA produced by the ATH1 gene, wherein the ATH1 gene comprises the nucleotide sequence of SEQ ID NO. 1.

4. A process as claimed in claim 1 whereby the flowering process in plants is retarded by transforming the plants using a construct that promotes the production of the ATH1 protein, wherein the ATH1 protein is encoded by the nucleotide sequence of SEQ ID NO. 1.

* * * * *

SEQUENCE LISTING

<160> NUMBER OF SEQ ID NOS: 2

<210> SEQ ID NO 1
<211> LENGTH: 1886
<212> TYPE: DNA
<213> ORGANISM: Arabidopsis Thaliana

<400> SEQUENCE: 1

```
atttagttat aaaatgttgc tatttgttga tctagtgctc tgaatctttt agtgaggcag      60
atgatgaaga ttatgaattt cttcatgaaa ttattgtaag aaaagaaca tagagaagct     120 gcggaatgaa agtacactgt tctttcacgg agaaagaaga taaataagca ttatcttctt     180
cttcagtttt taacacacat tttggaaatt ttgatgtaaa aattctcttt ggaacgttgt     240
gttgtctgaa atcttcccaa aggttctatc agaagaagaa ggataaagtt tcatagaaac     300
ccaatggaca acaacaacaa caacaacact tttagttctc tggataatgt catgactaac     360
caaaatcctc ttctcatgga ttttatacct tcaagagaag attcaacttc attctcaaca     420
atgcttccat ggaataccat cagatcagat cctctacaaa tgggtggctt tgatattttc     480
aattctatgc tgactaacaa atacttatca tcttctccac ggtctatcga tgttcaagat     540
aaccgcaatg ttgagttcat ggctcctcct cctcatcctc ctccacttca tcctttggat     600
catttaagac actatgatga ttcctcaaac aacatgtggg gttttgaagc aaatagtgag     660
```

```
-continued tttcaggcat tttcaggtgt agttggtcca agtgaaccaa tgatgtctac attcggtgaa    720
gaagatttcc cgtttctaat ttcgaataaa agaaacaatg agctttcatt gagtcttgca    780
tcagatgttt ctgatgaatg ctcggagata agtctttgtg cagctacaag attagcctca    840
gagcaagctt cttgcagcag caaagacatt tctaataacg ttgttactca aggtttctct    900
caacttatat ttggctcaaa ataccttcac tctgttcaag aaatactatc tcatttcgcc    960
gcatactcgc tcgattattc atctcgagga accgagtcag gagctgctag ttcagccttt   1020
acttcacgtt ttgagaatat aactgagttt cttgatggtg attctaataa ctcggaggcg   1080
ggtttcggat ctacatttca aaggagagca ttagaagcaa agaaaaccca tctcttggat   1140
cttcttcaaa tggtggatga tcgatatagt cattgcgtag atgagattca tacggttata   1200
tcagcgttcc atgctgcaac cgagttagat ccacagttac acacccggtt tgccctccaa   1260
accgtttcct tcttatacaa gaacctgaga gagagaatct gcaagaagat aatctctatg   1320
ggatctgtat tggagagagg caaagacaag actcaagaaa cctctatgtt ccaccagcat   1380
tgccttcttc agcagctgaa acgaaagaac catcagattt ggagacctca acgaggtttg   1440
cctgagaaat ctgtttcggt tctacggaat tggatgttcc aaaacttcct tcacccttac   1500
ccgaaagatt cggagaaaca tcttctagct atacgaagtg gcttgacaag aagtcaggta   1560
tcaaactggt ttataaatgc gcgggttagg ctatggaagc cgatgataga agagatgtat   1620
gcggaaatga acaagaggaa gctcaataac agtcacattc aacccaacgg accaactctt   1680
cgaatgccaa aatctgttat gatgagccaa gcaatgcata aataagacaa caattgtgtt   1740
taccaacttt gtgataatta ggcaattgct actctatgat tgcccaaaac ctaaaccatg   1800
tacgactatc attacgtatg ttataattgt atatacaact cctttatctt tgactatttc   1860
attttattaa aaaaaaaaa aaaaaa                                          1886

<210> SEQ ID NO 2
<211> LENGTH: 50
<212> TYPE: DNA
<213> ORGANISM: Artificial Sequence
<220> FEATURE:
<223> OTHER INFORMATION: Linker

<400> SEQUENCE: 2
ggaattctgg tacctcccgg gaggatccat ctagagctcg agtaagcttc                50
```